(12) United States Patent
Dryden et al.

(10) Patent No.: US 7,604,929 B2
(45) Date of Patent: Oct. 20, 2009

(54) CELLULAR COMPOSITIONS AND METHODS FOR THEIR PREPARATION

(75) Inventors: Daniel Dryden, Westminter, MD (US); James Hardy, Ijamsville, MD (US)

(73) Assignee: In Vitro Technologies, Inc., Baltimore, MD (US)

( * ) Notice: Subject to any disclaimer, the term of this patent is extended or adjusted under 35 U.S.C. 154(b) by 318 days.

(21) Appl. No.: 11/110,879

(22) Filed: Apr. 21, 2005

(65) Prior Publication Data

US 2005/0239042 A1    Oct. 27, 2005

(51) Int. Cl.
*A01N 1/00* (2006.01)
*C12N 5/00* (2006.01)
*C12N 5/08* (2006.01)

(52) U.S. Cl. .................. 435/1.1; 435/1.3; 435/370; 435/374; 435/375

(58) Field of Classification Search ............... 435/1.1, 435/1.3, 370, 374, 375
See application file for complete search history.

(56) References Cited

U.S. PATENT DOCUMENTS

| 5,795,711 | A | 8/1998 | Mullon et al. |
| 5,895,745 | A | 4/1999 | Chandler et al. |
| 6,136,525 | A | 10/2000 | Mullon et al. |
| 6,759,245 | B1 | 7/2004 | Toner et al. |
| 2002/0039786 | A1 | 4/2002 | Reid et al. |
| 2003/0134418 | A1 | 7/2003 | Mitaka |

FOREIGN PATENT DOCUMENTS

| EP | 0834252 B | 4/1998 |
| WO | WO92/12722 | 8/1992 |
| WO | WO/0153462 | 7/2001 |
| WO | WO03/105663 | 12/2003 |
| WO | WO2004/009766 | 1/2004 |
| WO | WO2005/000376 | 1/2005 |

OTHER PUBLICATIONS

Ostrowska et al., Cell and Tissue Banking, 2000, 1: 55-68.*
Shibata et al., Drug Metabolism and Disposition, 2002, 30: 892-896.*
Oehninger et al., Mol Cell Endocrinol, 2000, 169: 3-10.*
Hengstler et al., Drug Metab. Rev., 2000, 32: 81-118, Abstract.*
Arikura et al., UW solution: a promising tool for cryopreservation of primarily isolated rat hepatocytes, 9 J. Hepatobiliary Pancreat. Surg. 742-749 (2002).
Marsh et al., Hypothermic Preservation of Hepatocytes III Effects of Resuspension Media on Viability after up to 7 Days of Storage, 13(3) Hepatology 500-508 (1991).
Smrzova et al., Optimisation of Porcine Hepatocyte Cryopreservation by Comparison of Viability and Enzymatic Activity of Fresh and Cryopreserved Cells, 70 Acta Vet. Bmo. 141-147 (2001).
Vincent et al., Adjustment of the Osmolality of Percoll for the Isopycnic Separation of Cells and Cell Organelles, 141 Analytical Biochemistry 322-328 (1984).

Adams, R.M. et al. (1995) "*Effective Cryopreservation And Long-Term Storage Of Primary Human Hepatocytes With Recovery Of Viability, Differentiation, And Replicative Potential*," Cell Transplant. 4(6):579-586.
Alexandre, E. et al. (2002) "*Cryopreservation Of Adult Human Hepatocytes Obtained From Resected Liver Biopsies*," Cryobiology 44:103-113.
Anand, A.C. (1996) "*Bioartificial Livers: The State Of The Art*," Trop Gastroenterol. 17(4):197-198, 202-211.
Berry, M.N. et al. (1992) "*Techniques for Pharmacological And Toxicological Studies With Isolated Hepatocyte Suspensions*," Life Sci. 51(1):1-16.
Burlina, A.B. (2004) "*Hepatocyte Transplantation For Inborn Errors Of Metabolism*," J. Inherit. Metab. Dis. 27(3):373-83.
Chan, C. et al. (2004) "*Hepatic Tissue Engineering For Adjunct And Temporary Liver Support: Critical Technologies*," Liver Transpl. 10(11):1331-1342.
Chesne, C. et al. (1993) "*Viability And Function In Primary Culture Of Adult Hepatocytes From Various Animal Species And Human Beings After Cryopreservation*," Hepatology 18(2):406-414.
Coundouris, J.A. et al. (1993) "*Cryopreservation Of Human Adult Hepatocytes For Use In Drug Metabolism And Toxicity Studies*," Xenobiotica. 23(12):1399-1409.
Diener, B. et al. (1993) "*A Method For The Cryopreservation Of Liver Parenchymal Cells For Studies Of Xenobiotics*," Cryobiology 30(2):116-127.
Dou, M. et al. (1992) "*Thawed Human Hepatocytes In Primary Culture*," Cryobiology 29(4):454-69.
Fox, I.J. et al. (2004) "*Hepatocyte Transplantation*," Am. J. Transplant.4 Suppl. 6:7-13.
Fukuda, J. et al. (2004) "*Hepatocyte Organoid Culture In Elliptic Hollow Fibers To Develop A Hybrid Artificial Liver*," Int J Artif Organs. 27(12):1091-1099.
Gan, J.H. et al. (2005) "*Hybrid Artificial Liver Support System For Treatment of Severe Liver Failure*," World J Gastroenterol. 11(6):890-894.
Gomez-Lechon, M.J. et al. (2004) "*Human Hepatocytes In Primary Culture: The Choice To Investigate Drug Metabolism in Man*," Curr Drug Metab. 5(5):443-462.
Guillouzo, A. et al. (1986) "*Isolated and Cultured Hepatocytes*," Paris: les Editions INSERM and London: John Libbey Eurotext).
Hewitt, N.J. et al. (2004) *Cryopreserved Rat, Dog and Monkey Hepatocytes: Measurement Of Drug Metabolizing Enzymes In Suspensions And Cultures*, Hum Exp Toxicol. 23(6)307-316.
Horslen, S.P. (2004) "*Hepatocyte Transplantation*," Transplantation 77(10):1481-1486.
Houle, r. et al. (2003) "*Retention Of Transporter Activities in Cryopreserved, Isolated Rat Hepatocytes*," Drug Metab. Disposit. 31(4):447-451.
Kasai, s. et al. (1993) "*Large Scale Cryopreservation of Isolated Dog Hepatocytes*," Cryobiology 30:1-11.

(Continued)

*Primary Examiner*—Ileana Popa
(74) *Attorney, Agent, or Firm*—Loeb & Loeb LLP

(57) ABSTRACT

The present invention relates to novel cell (e.g., hepatocyte, etc.) compositions and methods for their preparation and use. In particular, the invention concerns methods of processing preparations of such cells so as to permit their repeated cryopreservation and thawing while retaining substantial viability. The invention also concerns preparations of cells (e.g., hepatocytes) that have been repeatedly cryopreserved and thawed.

11 Claims, No Drawings

OTHER PUBLICATIONS

Lawrence, J.N. et al. (1991) "*Development Of An Optimal Method For The Cryopreservation Of Hepatocytes And Their Subsequent Monolayer Culture. Toxicology* In Vitro," 5(1):39-51.

Lee, S. W. et al. (2004) "*Hepatocyte Transplantation: State Of The Art And Strategies For Overcoming Existing Hurdles,*" Ann. Hepatol. 3(2):48-53.

Lemaigre, F. et al. (2004) "*Liver Development Update: New Embryo Models, Cell Lineage Control, And Morphogenesis,*" Curr Opin Genet Dev. 14(5):582-590.

Li, A.P. et al. (1992) "*Isolation And Culturing Of Hepatocytes From Human Liver,*" J. Tissue Cult. Meth. 14:139-146.

Li, A.P. et al. (1999) "*Cryopreserved Human Hepatocytes: Characterization Of Drug-Metabolizing Enzyme Activities And Applications In Higher Throughput Screening Assays For Hepatotoxicity, Metabolic Stability, And Drug-Drug Interaction Potential,*" Chem Biol Interact. 121(1):17-35.

Li, A.P. et al. (1999) "*Present Status Of The Application Of Cryopreserved Hepatocytes In The Evaluation Of Xenobiotics: Consensus Of An* International *Expert Panel,*" Chem Biol Interact. 121(I):117-123.

Lloyd, T.D.R. et al. (2003) *Cryopreservation Of Hepatocytes: A Review Of Current Methods For Banking, Cell and Tissue Culture Banking* 4:3-15.

Loretz, L.J. et al. (1989) "*Optimization Of Cryopreservation Procedures For Rat And Human Hepatocytes,*" Xenobiotica. 19(5):489-498.

Madan, A. et al. (1999)"*Effect of Cryopreservation on Cytochrome P-450 Enzyme Induction in Cultured Rat Hepatocytes,*" Drug Metab. Dispos. 27(3):327-335.

Meng, Q. et al. (2004) "*Hepatocyte Culture In Bioartificial Livers With Different Membrane Characteristics,*" Biotechnol Lett. 26(18):1407-1412.

Morsiani et al., (1995) "*Automated Liver Cell Processing Facilitates Large Scale Isolation And Purification Of Porcine Hepatocytes,*" ASAIO Journal 41:155-161.

Nanji, A.A. (2004) "*Animal Models Of Nonalcoholic Fatty Liver Disease And Steatohepatitis,*" Clin Liver Dis. 8(3):559-574.

Novicki, D.L. et al. (1982) "*Cryopreservation Of Isolated Rat Hepatocytes,*" In Vitro. 18(4):393-399.

O'Brien, Z.Z. et al. (undated) "*The Construction Of A Representative Human Cryopreserved Hepatocyte Pool For Metabolism Study,*".

Ponsoda, X. et al. (2004) "*Drug Metabolism By Cultured Human Hepatocytes: How Far Are We From The* In Vivo *Reality?*" Altern Lab Anim. 32(2): 101-110.

Postic, C. et al. (2004) "*Role Of The Liver In The Control Of Carbohydrate And Lipid Homeostasis,*" Diabetes Metab. 30(5):398-408.

Roymans, D. et al. (2004) "*Determination Of Cytochrome P450 1A2 And Cytochrome P4503a4 Induction In Cryopreserved Human Hepatocytes,*" Biochem Pharmacol. 67(3):427-437.

Ruegg, C.E. et al. (1997) "*Cytochrome-P450 Induction and Conjugated Metabolism In Primary Human Hepastocytes After Cryopreservation,*" In Vitro Toxicol. 10:217-222.

Seglen, P.O. (1976) "*Preparation Of Isolated Rat Liver Cells,*" Meth. Cell Biol. 13:29-83).

Sekido, H. el al. (2004) "*Usefulness Of Artificial Liver Support For Pretransplant Patients With Fulminant Hepatic Failure,*" Transplant Proc. 36(8):2355-2356.

Shaddock, J,G. et al. (1993) "*Cryopreservation And Long-Term Storage Of Primary Rat Hepatocytes: Effects On Substrate-Specific Cytochrome P450-Dependent Activities And Unscheduled DNA Synthesis,*" Cell Biol Toxicol. 9(4):345-357.

Silva, J.M. et al. (1999) "*Induction Of Cytochrome-P450 In Cryopreserved Rat And Human Hepatocytes,*" Chem-Biol Interact 121:49-63.

Sun, E.L. et al. (1990) "*Cryopreservation Of Cynomologus Monkey (Macaca fascicularis) Hepatocytes For Subsequent Culture And Protein Synthesis Studies,*" In vitro *Cell Development and Biology* 25:147-150.

Utesch, D. et al. (1992) "*Characterization Of Cryopreserved Rat Liver Parenchymal Cells By Metabolism Of Diagnostic Substrates And Activities Of Related Enzymes,*" Biochemical Pharmacology 44:309-315.

Zaleski, J. et al. (1993) "*Preservation Of The Rate And Profile Of Xenobiotic Metabolism In Rat Hepatocytes Stored In Liquid Nitrogen,*" Biochem Pharmacol. 46(1):111-116.

Zhang, J.G. et al. (undated) "Validation of Pooled Cryopreserved Human Hepatocytes as a Model for Metabolism Studies" www.Bdbiosciences.com.

Li et al., Present status of the application of cryopreserved hepatocytes in the evaluation of xenobiotics . . . , 121 Chemico-Biological Interactions 117-123 (1999).

Li, Overview: hepatocytes and cryopreservation—a personal historical perspective, 121 Chemico-Biological Interactions 1-5 (1999).

* cited by examiner

CELLULAR COMPOSITIONS AND METHODS FOR THEIR PREPARATION

FIELD OF THE INVENTION

The present invention relates to novel cell (e.g., hepatocyte, etc.) compositions and methods for their preparation and use. In particular, the invention concerns methods of processing preparations of such cells so as to permit their repeated cryopreservation and thawing while retaining substantial viability. The invention also concerns preparations of cells (e.g., hepatocytes) that have been repeatedly cryopreserved and thawed.

BACKGROUND OF THE INVENTION

Hepatocytes are parenchymal liver cells, and make up 60-80% of the cytoplasmic mass of the liver. Hepatocytes play a key role in the detoxification, modification and excretion of exogenous and endogenous substances (Ponsoda, X. et al. (2004) "*Drug Metabolism By Cultured Human Hepatocytes: How Far Are We From The In Vivo Reality?*" Altern Lab Anim. 32(2): 101-110). One of the detoxifying functions of hepatocytes is to modify ammonia to urea for excretion. They are also important in protein synthesis and storage, in the transformation of carbohydrates and in the synthesis of cholesterol, bile salts and phospholipids (Postic, C. et al. (2004) "*Role Of The Liver In The Control Of Carbohydrate And Lipid Homeostasis*," Diabetes Metab. 30(5):398-408). The hepatocyte is the only cell in the body that manufactures albumin, fibrinogen, and the prothrombin group of clotting factors. It is the main site for the synthesis of lipoproteins, ceruloplasmin, transferrin, and glycoproteins. Hepatocytes manufactures their own structural proteins and intracellular enzymes. Hepatocytes are also important depots for vitamin B12 and iron.

Due to these attributes, isolated and cultured hepatocytes have become very attractive as models systems for the study of liver functions (Chesne, C. et al. (1993) "*Viability And Function In Primary Culture Of Adult Hepatocytes From Various Animal Species And Human Beings After Cryopreservation*," Hepatology 18(2):406-414; Guillouzo, A. et al. (1986) "*Isolated and Cultured Hepatocytes*," Paris: les Editions INSERM and London: John Libbey Eurotext); Ponsoda, X. et al. (2004) "*Drug Metabolism By Cultured Human Hepatocytes: How Far Are We From The In Vivo Reality?*" Altern Lab Anim. 32(2): 101-110; Gomez-Lechon, M. J. et. al. (2004) "*Human Hepatocytes In Primary Culture: The Choice To Investigate Drug Metabolism In Man*," Curr Drug Metab. 5(5):443-462; Lemaigre, F. et al. (2004) "*Liver Development Update: New Embryo Models, Cell Lineage Control, And Morphogenesis*," Curr Opin Genet Dev. 14(5):582-590; Nanji, A. A. (2004) "*Animal Models Of Nonalcoholic Fatty Liver Disease And Steatohepatitis*," Clin Liver Dis. 8(3):559-574; Hewitt, N. J. et al. (2004) *Cryopreserved Rat, Dog And Monkey Hepatocytes: Measurement Of Drug Metabolizing Enzymes In Suspensions And Cultures*," Hum Exp Toxicol. 23(6):307-316).

In addition to their use in liver models, hepatocytes have the potential of being used to produce Bioartificial Livers (BALs) or in hepatocyte transplantation that can provide liver functions for individuals suffering from liver disease or liver failure. Bioartificial Livers (BALs) are described by Anand, A. C. (1996) "*Bioartificial Livers: The State Of The Art*," Trop Gastroenterol. 17(4):197-198, 202-211; Gan, J. H. et al. (2005) "*Hybrid Artificial Liver Support System For Treatment Of Severe Liver Failure*," World J Gastroenterol. 11 (6):890-894; Fukuda, J. et al. (2004) "*Hepatocyte Organoid Culture In Elliptic Hollow Fibers To Develop A Hybrid Artificial Liver*," Int J Artif Organs. 27(12): 1091-1099; Meng, Q. et al. (2004) "*Hepatocyte Culture In Bioartificial Livers With Different Membrane Characteristics*," Biotechnol Lett. 26(18): 1407-1412; Sekido, H. et al. (2004) "*Usefulness Of Artificial Liver Support For Pretransplant Patients With Fulminant Hepatic Failure*," Transplant Proc. 36(8):2355-2356; WO03/105663A2, WO05/000376A2, and U.S. Pat. No. 6,759,245. Hepatocyte transplantation is described by Chan, C. et al. (2004) "*Hepatic Tissue Engineering For Adjunct And Temporary Liver Support: Critical Technologies*," Liver Transpl. 10(11): 1331-1342; Lee, S. W. et al. (2004) "*Hepatocyte Transplantation: State Of The Art And Strategies For Overcoming Existing Hurdles*," Ann. Hepatol. 3(2):48-53; Horslen, S. P. (2004) "*Hepatocyte Transplantation*," Transplantation 77(10):1481-1486; Burlina, A. B. (2004) "*Hepatocyte Transplantation For Inborn Errors Of Metabolism*," J. Inherit. Metab. Dis. 27(3):373-83; and Fox, I. J. et al. (2004) "*Hepatocyte Transplantation*," Am. J. Transplant. 4 Suppl. 6:7-13.

A limiting factor in the development of such model systems and to the development of Bioartificial Livers (BALs) has been the erratic source and limited availability of hepatocytes, especially human hepatocytes. Fresh hepatocytes are obtainable only from liver resections or non-transplantable livers of multi-organ donors (Lloyd, T. D. R. et al. (2003) *Cryopreservation Of Hepatocytes: A Review Of Current Methods For Banking*," Cell and Tissue Culture Banking 4:3-15). The supply of such tissue is inconsistent and often geographically inconvenient in light of the limited functional lifespan of liver tissue (Smrzova, J. et al. (2001) "*Optimization Of Porcine Hepatocytes Cryopreservation By Comparison Of Viability And Enzymatic Activity Of Fresh And Cryopreserved Cells*," Acta Veterinaria Brunensis 70:141-147).

One approach to addressing this problem has involved the development of hepatocyte storage conditions that allow hepatocytes to be maintained over time with their cellular functions preserved. Cryopreservation methods for the storage of hepatocytes have been developed to address this need (see, Lloyd, T. D. R. et al. (2003) *Cryopreservation Of Hepatocytes: A Review Of Current Methods For Banking*," Cell and Tissue Culture Banking 4:3-15; Loretz, L. J. et al. (1989) "*Optimization Of Cryopreservation Procedures For Rat And Human Hepatocytes*," Xenobiotica. 19(5):489-498; Shaddock, J, G. et al. (1993) "*Cryopreservation And Long-Term Storage Of Primary Rat Hepatocytes: Effects On Substrate-Specific Cytochrome P450-Dependent Activities And Unscheduled DNA Synthesis*," Cell Biol Toxicol. 9(4):345-357; Novicki, D. L. et al. (1982) "*Cryopreservation Of Isolated Rat Hepatocytes*," In Vitro. 18(4):393-399; Zaleski, J. et al. (1993) "*Preservation Of The Rate And Profile Of Xenobiotic Metabolism In Rat Hepatocytes Stored In Liquid Nitrogen*," Biochem Pharmacol. 46(1):111-116). Typically, such measures comprise storage in liquid nitrogen (−196° C.) or in frozen nitrogen gas (−150° C.). The ability to recover viable thawed cells has been found to depend on multiple factors such as the rate of freezing, the concentration of hepatocytes, the type of cryoprotectant employed, and the final cooling temperature. Cell concentrations of $10^6$-$10^7$ cells/ml have been typically employed. The isolated hepatocytes are typically incubated in suspension for a period (e.g., 4-48 hours) to allow them to recover from the isolation process. Thereafter, a cryoprotectant (such as glycerol, DMSO, polyvinylpyrrolodine, or dextran) is added, and the hepatocytes are frozen. The art has developed various freezing procedures, all designed to minimize or prevent the occurrence of intracellular ice. The freezing rates typically vary from −0.05° C./min to −50° C./min (see, Lloyd, T. D. R. et al. (2003) *Cryopreservation Of Hepatocytes: A Review Of Current Methods For Banking,*" *Cell and Tissue Culture Banking* 4:3-15).

While the development of cryopreservation methods for the storage of hepatocytes has significantly facilitated the availability of human hepatocytes, cryopreservation has been found to cause a significant decrease in cellular viability (e.g., 25-35%) (Dou, M. et al. (1992) "*Thawed Human Hepatocytes In Primary Culture,*" Cryobiology 29:454-469; Alexandre, E. et al. (2002) "*Cryopreservation Of Adult Human Hepatocytes Obtained From Resected Liver Biopsies,*" Cryobiology 44:103-113). Coundouris, J. A. et al. (1993) reported viability of 67% after 24 hours, declining to 49% after 14 days (Coundouris, J.A. et al. (1993) "*Cryopreservation Of Human Adult Hepatocytes For Use In Drug Metabolism And Toxicity Studies,*" Xenobiotica. 23(12):1399-1409). Adams, R. M. et al. have reported that the viability of hepatocytes may be enhanced to greater than 90% using specialized cyropreservation fluids, however, only 16% of cells were found to be capable of replication (Adams, R. M. et al. (1995) "*Effective Cryopreservation And Long-Term Storage Of Primary Human Hepatocytes With Recovery Of Viability, Differentiation, And Replicative Potential,*" Cell Transplant. 4(6):579-586). Methods of cryopreservation are disclosed in U.S. Pat. Nos. 5,795,711, 6,136,525, 5,895,745; International Patent Publications WO04/009766, WO92/12722, WO/0153462, European Patent No. EP0834252B, and U.S. Patent Application Publication Nos. US20020039786A1, US20030134418A1. The poor recovery of cells when cryopreserved continues to limit the use of hepatocytes in in vitro liver models.

A second major problem affecting the use of both fresh and cryopreserved hepatocytes is the variation of liver enzyme expression that is observed in tissue from different donors (Li, A. P. et al. (1999) "*Present Status Of The Application Of Cryopreserved Hepatocytes In The Evaluation Of Xenobiotics: Consensus Of An International Expert Panel,*" Chem Biol Interact. 121(1):117-123; Li, A. P. et al. (1999) "*Cryopreserved Human Hepatocytes: Characterization Of Drug-Metabolizing Enzyme Activities And Applications In Higher Throughput Screening Assays For Hepatotoxicity, Metabolic Stability And Drug-Drug Interaction Potential,*" Chem Biol Interact. 121(1):17-35; O'Brien, Z. Z. et al. (undated) "*The Construction Of A Representative Human Cryopreserved Hepatocyte Pool For Metabolism Study.*" One solution to this sample variation involves pooling samples from different sources to produce a "composite" hepatocyte preparation having the characteristics of "average" liver cells. However, the frequency of receipt of fresh tissue and the need to cryopreserve hepatocytes immediately after isolation has been cited as preventing the preparation of hepatocyte pools. Thus, multiple companies (e.g., Xenotech, LLC; BD Biosciences) refrain from selling pooled hepatocytes thus forcing the end user to thaw and pool hepatocytes from several different donors. This difficulty remains even though pooled cryopreserved human hepatocytes are a valid model for metabolic studies (Zhang, J. G. et al. (undated) "*Validation Of Pooled Cryopreserved Human Hepatocytes As A Model For Metabolic Studies.*"

Thus, despite all prior advances, a need remains for processes that would enable the availability of hepatocytes for medical research and other purposes. A need further exists for a stable and reproducible source of human hepatocytes. The present invention permits the production and availability of hepatocyte preparations that may be repeatedly cryopreserved and thawed without unacceptable loss of viability. The invention thus permits multiple hepatocyte samples to be pooled to produce pooled hepatocyte preparations, especially pooled cryopreserved human hepatocyte preparations. Using such advance, pooled cryopreserved human hepatocytes are now commercially available from In Vitro Technologies (Baltimore, Md.).

SUMMARY OF THE INVENTION

The present invention relates to novel cell (e.g., hepatocyte) compositions and methods for their preparation and use. In particular, the invention concerns methods of processing preparations of cells, especially hepatocytes, so as to permit their repeated cryopreservation and thawing while retaining substantial viability. The invention also concerns preparations of cells (e.g., hepatocytes) that have been repeatedly cryopreserved and thawed.

In detail, the invention particularly concerns a multi-cryopreserved hepatocyte preparation comprising hepatocytes that have been frozen and thawed at least two times, wherein greater than 50% and more preferably 70% or more of the hepatocytes of the preparation are viable.

The invention further concerns the embodiment of such a multi-cryopreserved hepatocyte preparation wherein the hepatocytes are selected from the group consisting of human hepatocytes, porcine hepatocytes, simian hepatocytes, canine hepatocytes, feline hepatocytes, bovine hepatocytes, equine hepatocytes, ovine hepatocytes and rodent hepatocytes.

The invention further concerns the embodiment of such a multi-cryopreserved hepatocyte preparation wherein the preparation comprises a pooled preparation of hepatocytes of multiple sources, which may be of the same or different gender, race, or health state, or which provide the pooled preparation with a desired level of a metabolic activity (especially wherein the metabolic activity is selected from the group consisting of COUM, DEX, ECOD, 7-HCG, 7-HCS, MEPH, TEST, PHEN and CZX).

The invention further concerns a method of producing a desired preparation of multi-cryopreserved hepatocytes, the hepatocytes being capable of being frozen and thawed at least two times, and in which greater than 50% and more preferably 70% or more of the hepatocytes of the preparation are viable, the method comprising:
(A) subjecting hepatocytes that have been frozen and thawed to density gradient fractionation (especially percoll density centrifugation) to separate viable hepatocytes from non-viable hepatocytes,
(B) recovering the separated viable hepatocytes, and
(C) cryopreserving the recovered viable hepatocytes to thereby form the desired preparation of hepatocytes.

The invention further concerns the embodiment of such a method in which the hepatocytes are selected from the group consisting of human hepatocytes, porcine hepatocytes, simian hepatocytes, canine hepatocytes, feline hepatocytes, bovine hepatocytes, equine hepatocytes, ovine hepatocytes and rodent hepatocytes.

The invention further concerns the embodiment of such a method in which the preparation comprises a pooled preparation of hepatocytes of multiple sources, which may be of the same or different gender, race, or health state, or which provide the pooled preparation with a desired level of a metabolic activity (especially wherein the metabolic activity is selected from the group consisting of COUM, DEX, ECOD, 7-HCG, 7-HCS, MEPH, TEST, PHEN and CZX).

The invention also concerns a method of investigating in vitro drug metabolism comprising incubating hepatocytes of a multi-cryopreserved hepatocyte preparation in the presence of a xenobiotic, and determining the metabolic fate of the xenobiotic, or the effect of the xenobiotic on the hepatocytes or on an enzyme or metabolic activity thereof, wherein the hepatocytes have been frozen and thawed at least two times, and wherein greater than 50% and more preferably 70% or more of the hepatocytes of the preparation are viable.

DESCRIPTION OF THE PREFERRED EMBODIMENTS

The present invention relates to novel cell compositions and methods for their preparation and use. In particular, the invention concerns methods of processing preparations of cells so as to permit their repeated cryopreservation and thawing while retaining substantial viability. The methods of the present invention are generally applicable to a wide variety of cell types, including hepatocytes, kidney cells, spleen cells, thymus cells, bone marrow cells, stem cells, muscle cells (including cardiac muscle cells), endocrine cells (including pancreatic cells, adrenal cells, thyroid cells, etc.) epidermal cells, endodermal cells, etc. The methods of the present invention are illustrated below with respect to a preferred cell type: hepatocytes.

The invention also concerns preparations of cells, e.g., hepatocytes, that have been repeatedly cryopreserved and thawed to obtain a high viability preparation useful for a variety of experimental, diagnostic and therapeutic purposes. The present invention extends the ability of hepatocytes to be cryopreserved and thawed for later use, so as to permit hepatocyte preparations to be repeatedly cryopreserved and thawed without an unacceptable loss of viability.

As used herein, the term "cell preparation" denotes a liquid or frozen composition of cells from one or more sources (e.g., "hepatocyte preparation" denotes a composition of liver cells from one or more sources). The sources may be primary cells that have been dissociated from or isolated from tissue as by resection, biopsy, or from donor organs, or they may be secondary, immortalized or transformed cell cultures. The cells may be derived from any mammalian source, including human, porcine, simian, canine, feline, bovine, equine, ovine or rodent sources. The use of human, porcine or rodent (especially rat) cells is preferred. Preferably, greater than 50% and more preferably 70% or more of the hepatocytes of such preparations will be viable.

As used herein, the term "multi-cryopreserved cell preparation" denotes a cell preparation that has been frozen and then thawed at least two times (e.g., a "multi-cryopreserved hepatocyte preparation" denotes a hepatocyte preparation that has been frozen and then thawed at least two times). Such preparations may have been frozen and thawed three, four, five, or more times.

The term "pooled preparation" denotes a cell ( e.g., hepatocyte) preparation in which the cells (e.g., hepatocytes) are derived from two, three, four, five, or more different sources, such as different donors, biopsies, tissue resections from different tissue samples or different tissue sources, or different primary, secondary, immortalized or transformed cell (e.g., hepatocyte) cultures. The cells of such pooled preparations may be randomly selected cell, or may have been selected to provide the pooled preparation with a desired level of one or more metabolic activities (such as for example, a preparation of hepatocytes having a desired level of COUM, DEX, ECOD, 7-HCG, 7-HCS, MEPH, TEST, PHEN and/or CZX activity), or a desired cell characteristic (such as, for example, a preparation of hepatocytes derived from sources of the same gender, age, race (e.g., Caucasian, etc.), or health state (e.g., hepatocytes of hepatitis virus-infected liver, hepatocytes of HIV-1 infected liver, hepatocytes of healthy liver, hepatocytes of cigarette smokers, hepatocytes of individuals suffering from cirrhosis of the liver, or from other diseases or conditions). For example, to obtain a pooled hepatocyte preparation with minimal DEX activity, a pooled preparation could be prepared from Lot. Nos. 067, CEK, ETR, PFM, VTA, or WWM (see, Table III).

In a preferred embodiment, illustrated with respect to hepatocyte cells, the practice of the invention comprises some or all of the following steps: the isolation of hepatocytes, a first cryopreservation of the isolated primary hepatocytes to obtain a first cryopreserved hepatocyte preparation, the thawing of the first cryopreserved hepatocyte preparation to obtain viable hepatocytes, and the reformulation of the thawed viable hepatocytes to permit their further storage and use through repeated cryopreservation and thawing to obtain viable hepatocytes.

The Isolation of Hepatocytes

Any of a wide variety of methods may be employed or adapted to permit the isolation of the primary hepatocytes used in the present invention. For example, suitable techniques for the isolation of hepatocytes are outlined in Morsiani et al., (1995) "*Automated Liver Cell Processing Facilitates Large Scale Isolation And Purification Of Porcine Hepatocytes,*" *ASAIO Journal* 41:155-161 and in Seglen, P. O. (1976) "*Preparation Of Isolated Rat Liver Cells,*" Meth. Cell Biol. 13:29-83). Specific reference is made to the two-step collagenase digestion procedure described in Li, A. P. et al. (1992) "*Isolation And Culturing Of Hepatocytes From Human Liver,*" J. Tissue Cult. Meth. 14:139-146.

The hepatocytes may be cultured in any suitable hepatocyte culture medium. By way of illustration and not limitation mention may be made of the following culture media Chee's Essential Media (Hamilton, G. A. et al. (2001) "*Effects Of Medium Composition On The Morphology And Function Of Rat Hepatocytes Cultured As Spheroids And Monolayers,*" In Vitro Cell Dev Biol Anim. 37(10):656-667; Zurlo, J. et al. (1996) "*Characterization Of A Primary Hepatocyte Culture System For Toxicological Studies,*" In Vitro Cell Dev Biol Anim. 32(4):211-220; Arterburn, L. M. et al. (1995) "*A Morphological Study Of Differentiated Hepatocytes In Vitro,*" Hepatology 22(1):175-187), Modified Eagle Medium (or Dulbecco's Modified Eagle Medium) (Arikura, J. et al. (2002) "*UW Solution: A Promising Tool For Cryopreservation Of Primarily Isolated Rat Hepatocytes,*" J Hepatobiliary Pancreat Surg. 9(6):742-749; Washizu, J. et al. (2000) "*Amino Acid Supplementation Improves Cell-Specific Functions Of The Rat Hepatocytes Exposed To Human Plasma,*" Tissue Eng. 6(5):497-504; Iwata, H. et al. (1999) "*In Vitro Evaluation Of Metabolic Functions Of A Bioartificial Liver,*" ASAIO J. 45(4):299-306; Stutenkemper, R. et al. (1992) "*The Hepatocyte-Specific Phenotype Of Murine Liver Cells Correlates With High Expression Of Connexin32 And Connexin26 But Very Low Expression Of Connexin43,*" Exp Cell Res. 201(1): 43-54), Leibowitz medium (Coundouris, J. A. et al. (1993) "*Cryopreservation Of Human Adult Hepatocytes For Use In Drug Metabolism And Toxicity Studies,*" Xenobiotica. 23(12):1399-1409), Waymouth (Vind, C. et al. (1992) "*Regulation By Growth Hormone And Glucocorticoid Of Testosterone Metabolism In Long-Term Cultures Of Hepatocytes From Male And Female Rats,*" Biochem Pharmacol. 44(8):1523-1528; Nemoto, N. et al. (1991) "*Proline Is Required For Transcriptional Control Of The Aromatic Hydrocarbon-Inducible P(1)450 Gene In C57BL/6 Mouse Monolayer-Cultured Hepatocytes,*" Jpn J Cancer Res. 82(8):901-908; Dich, J. et al. (1988) "*Long-Term Culture Of Hepatocytes: Effect Of*

Hormones On Enzyme Activities And Metabolic Capacity," Hepatology. 8(1):39-45; Goethals, F. et al. (1984) "Critical Biochemical Functions Of Isolated Hepatocytes As Sensitive Indicators Of Chemical Toxicity," Fundam Appl Toxicol. 4(3 Pt 1):441-450), Kreb's medium (House, J. D. (2001) "Threonine Metabolism In Isolated Rat Hepatocytes," Am J Physiol Endocrinol Metab. 281(6):E1300-1307; Irvine, F. et al. (1993) "Extracellular Calcium Modulates Insulin's Action On Enzymes Controlling Cyclic AMP Metabolism In Intact Hepatocytes," Biochem J. 293 (Pt 1):249-253; Marsh, D. C. et al. (1991) "Hypothermic Preservation Of Hepatocytes. III. Effects Of Resuspension Media On Viability After Up To 7 Days Of Storage," Hepatology 13(3):500-508), etc.

In a preferred embodiment, hepatocytes are cryopreserved in a medium containing approximately 10% DMSO and approximately 90% fetal bovine serum (Loretz, L. J. et al. (1989) "Optimization Of Cryopreservation Procedures For Rat And Human Hepatocytes," Xenobiotica 19:489-498; Ruegg, C. E. et al. (1997) "Cytochrome-P450 Induction and Conjugated Metabolism In Primary Human Hepastocytes After Cryopresevation," In Vitro Toxicol. 10:217-222).

The viability of the isolated hepatocytes may be determined using any of a variety or methods. Preferable, such viability will be determined using the Trypan blue exclusion method (see, e.g., Berry, M. N. et al. (1992) "Techniques For Pharmacological And Toxicological Studies With Isolated Hepatocyte Suspensions," Life Sci. 51(1):1-16). Thus the phrases "viable hepatocytes" or "percent viability", as used herein, refers to hepatocyte viability as assessed using the method of Trypan Blue exclusion.

Cryopreservation of the Isolated Primary Hepatocytes

The hepatocytes of the present invention are preferably cryopreserved using liquid nitrogen, and most preferably within 36 hours of their isolation. Considerations for the cryopreservation of human hepatocytes are discussed in Lloyd, T. D. R. et al. (2003) Cryopreservation Of Hepatocytes: A Review Of Current Methods For Banking," Cell and Tissue Culture Banking 4:3-15. Suitable procedures for the cryopreservation of hepatocytes may also be found in the following documents: Adams, R. M. et al. (1995) "Effective Cryopreservation And Long-Term Storage Of Primary Human Hepatocytes With Recovery Of Viability, Differentiation, And Replicative Potential," Cell Transplant. 4(6):579-586; Chesne, C. et al. (1993) "Viability And Function In Primary Culture Of Adult Hepatocytes From Various Animal Species And Human Beings After Cryopreservation," Hepatology 18(2):406-414; Coundouris, J. A. et al. (1993) "Cryopreservation Of Human Adult Hepatocytes For Use In Drug Metabolism And Toxicity Studies," Xenobiotica. 23(12):1399-1409; Hewitt, N. J. et al. (2004) Cryopreserved Rat, Dog And Monkey Hepatocytes: Measurement Of Drug Metabolizing Enzymes In Suspensions And Cultures," Hum Exp Toxicol. 23(6):307-316; Novicki, D. L. et al. (1982) "Cryopreservation Of Isolated Rat Hepatocytes," In Vitro. 18(4):393-399; Shaddock, J, G. et al. (1993) "Cryopreservation And Long-Term Storage Of Primary Rat Hepatocytes: Effects On Substrate-Specific Cytochrome P450-Dependent Activities And Unscheduled DNA Synthesis," Cell Biol Toxicol. 9(4):345-357; Zaleski, J. et al. (1993) "Preservation Of The Rate And Profile Of Xenobiotic Metabolism In Rat Hepatocytes Stored In Liquid Nitrogen," Biochem Pharmacol. 46(1):111-116.

Preferably, isolated hepatocytes are suspended in a cryoprotective medium, and the suspended cells are dispensed into freezer-safe containers. A cryoprotective medium typically comprises a hepatocyte culture medium that contains at least one cryoprotectant that minimizes the deleterious effects of cryopreservation such as the formation of intracellular ice during freezing. By way of illustration and not limitation, the following commonly used cryoprotectants are listed: dimethylsulfoxide (DMSO), polyethylene glycol, amino acids, propanediol, and glycerol. A preferred cryoprotectant of the present invention is DMSO. Suitable cryoprotectants and methods for their use in hepatocyte cryopreservation can be found, for example, in: Loretz, L. J. et al. (1989) "Optimization Of Cryopreservation Procedures For Rat And Human Hepatocytes," Xenobiotica. 19(5):489-498; Chesne, C. et al. (1993) "Viability And Function In Primary Culture Of Adult Hepatocytes From Various Animal Species And Human Beings After Cryopreservation," Hepatology 18(2):406-414; Diener, B. et al. (1993) "A Method For The Cryopreservation Of Liver Parenchymal Cells For Studies Of Xenobiotics," Cryobiology 30(2):116-127; Lawrence, J. N. et al. (1991) "Development Of An Optimal Method For The Cryopreservation Of Hepatocytes And Their Subsequent Monolayer Culture. Toxicology In Vitro," 5(1):39-51; Houle, r. et al. (2003) "Retention of Transporter Activities in Cryopreserved. Isolated Rat Hepatocytes," Drug Metab. Disposit. 31(4):447-451; Silva, J. M. et al. (1999) "Induction Of Cytochrome-P450 In Cryopreserved Rat And Human Hepatocytes," Chem-Biol Interact 121:49-63.

The isolated hepatocytes are preferably suspended in a cryoprotective medium in preparation for freezing. The suspended cells are preferably dispensed into freezer resistant containers at a cell density of from about $10^6$ cells/ml to about $4 \times 10^7$ cells/ml. Preferred freezing volumes range from 0.1-10.0 ml. The preferred freezing volume is 1.0 ml.

The dispensed hepatocytes are then preferably cryopreserved using a controlled rate freezing process, most preferably at a freezing rate of between about $-1°$ C./min to about $-25°$ C./min until a final temperature of about $-90°$ C. is reached. During the initial phase of the cryopreservation process, seeding may be employed to induce controlled crystallization or ice formation in cell suspensions that have already been cooled to below the freezing point of the culture medium. Such seeding serves to minimize ice formation-related damage and therefore may be beneficial to cell viability. Suitable seeding methods include inserting a cold metal rod into the freezing containers, and introducing a blast of liquid nitrogen into the freezing containers.

Once the desired final temperature has been reached, the frozen cell samples may be transferred to liquid nitrogen freezers for prolonged storage. The frozen samples may be stored in either the liquid nitrogen phase or the gas phase of liquid nitrogen. Preferably storage is accomplished in the gas phase of liquid nitrogen. The frozen samples may be stored in this manner for days, months, or years, with the length of storage in the gas phase of liquid nitrogen having little effect on the post-thaw viability and function.

The Thawing of Cryopreserved Hepatocytes

Frozen samples may be thawed for further processing by removing them from the presence of liquid nitrogen or liquid nitrogen vapor. Frozen samples are preferably thawed by placing the samples immediately into a prewarmed water bath having a temperature of between about $37°$ C. to about $42°$ C. Preferably, cells are thawed to at least the stage in which ice chunks can be dislodged when the sample container is inverted. The thawed cells are then preferably rapidly processed to remove the cells from contact with DMSO, for example by PERCOLL® (colloidal silica particles of 15-30 nm diameter (23% w/w in water) which have been coated with polyvinylpyrrolidone (PVP)) gradient centrifugation (as described below) or by sequential washings.

In a preferred embodiment, the cells are thawed into Complete INVITROGRO™ CP medium (In Vitro Technologies, Baltimore, Md.; Roymans, D. et al. (2004) "*Determination Of Cytochrome P450 1A2 And Cytochrome P4503a4 Induction In Cryopreserved Human Hepatocytes*," Biochem Pharmacol. 67(3):427-437) (hepatocyte plating medium, which contains water, Dulbecco's Modified Eagle Medium, sodium bicarbonate, HEPES, fructose, bovine serum albumin, sodium hydroxide, MEM non-essential amino acids, insulin, hydrocortisone, and newborn calf serum). The medium is prepared by thawing TORPEDO™ Antibiotic Mix (In Vitro Technologies, Baltimore, Md.) (a mixture of antibiotics selected to inhibit bacterial growth in hepatocyte cell cultures that contains penicillin, streptomycin, gentamicin, amikacin and fungizone) to 37° C. in a water bath until thawed, and then removed from the water bath. 1.0 ml of TORPEDO™ Antibiotic Mix is then mixed with 45 ml INVITROGRO™ CP medium. Following the addition of TORPEDO™ Antibiotic Mix, the shelf life for the complete medium is 7 days. When thawing a single vial, the INVITROGRO™ CP medium is prewarmed to approximately 37° C. 5 ml of warmed INVITROGRO™ CP medium is added to a sterile 50 ml conical tube. The vial of frozen hepatocytes is carefully removed from the freezer. If the vial was stored in the liquid phase, its cap is carefully removed, any liquid nitrogen present in the vial is decanted, and the cap is reclosed before placing the vial into the water bath. It is preferred to then immediately immerse the vial into a 37° C. water bath, and to shake the vial gently until the ice is entirely melted, but no longer than it takes to completely thaw the vial. It may be helpful to remove any labels from the vial so that it will be easier to view the vial contents. The thawed contents are then emptied into the prewarmed INVITROGRO™ CP medium. 1.0 ml of prewarmed INVITROGRO™ CP medium then is added to each vial to resuspend any remaining cells. The contents of the vial are then decanted or pipetted into the hepatocyte suspension. The hepatocytes are preferably resuspended by gently inverting the receiving container (e.g., vial, test tube, etc.) several (e.g., three) times.

When thawing multiple vials, it is preferred that all of the vials be thawed in the water bath simultaneously. As before, the medium (preferably, INVITROGRO™ CP medium) should be warmed to 37° C. It is desirable to ensure that there is enough medium to permit 5 ml of pre-warmed INVITROGRO™ CP medium to be used for each vial of cryopreserved hepatocytes. After vials have thawed, their caps should be quickly removed and their contents poured into a sterile tube or beaker that contains at least 5 ml of pre-warmed INVITROGRO™ CP medium per vial thawed. For example, 25 ml of media is preferably employed for 5 vials in a container that can hold a volume of 50 ml.

If desired, the total cell count and the number of viable cells may be determined using the Trypan Blue exclusion method. Cells may be diluted to $0.70 \times 10^6$ viable cells/ml with INVITROGRO™ CP medium.

The Reformulation of Thawed Hepatocytes to Permit Further Cryopreservation and Thawing One aspect of the present invention concerns the ability to reformulate the thawed cells so that they may be refrozen and rethawed on one or more subsequent occasions. Such multi-cryopreserved hepatocyte preparations have multiple uses. They may be used in bioartificial livers, liver cell transplants, liver assist devices, hepatocyte transplantations, and in vitro applications. In particular, multi-cryopreserved hepatocyte preparations may be used in in vitro drug metabolism studies (for example, in identifying hepatocytes with unique characteristics (e.g.,. metabolic polymorphisms, genetic polymorphisms, etc.), in studies on the metabolic fate of the xenobiotic and studies on the affect of the xenobiotic in altering the drug-metabolizing enzyme profile of the hepatocytes, in inhibition studies to determine the $IC_{50}$ of xenobiotics on liver enzymes and functions (e.g. cholesterol metabolism), in gene induction studies with xenobiotics, in protein induction studies with xenobiotics, in toxicity assessment of xenobiotics on hepatocytes, transport studies with xenobiotics (e.g. studies on P-glycoprotein transport systems, organic ion transporters, organic cation transporters, etc.), in metabolic clearance studies with xenobiotics, and in efficacy assays (e.g. lipoprotein processing, gluconeogenesis, protein secretion etc.). Multi-cryopreserved hepatocyte preparations may also be used to study or propagate hepatitis viruses and other infectious viruses and agents. Recovered cells may be reformulated for use in DNA, mRNA or proteomic studies or in studies of metabolic polymorphisms. Multi-cryopreserved hepatocyte preparations may also be used in metabolic clearance studies and efficacy assays (e.g., lipoprotein processing, gluconeogenesis, protein secretion, etc.). Cells may be reformulated for use in seeding bioreactors for large scale incubations or as models for gene regulation via micro RNA, or for use in combination systems with other cell types (e.g. non-parenchymal cells from liver or cells from other sources, e.g. Caco-2 cells).

In a preferred embodiment of the invention, such reformulation comprises separating viable and non-viable cells prior to a subsequent refreezing. Density gradient centrifugation is preferably employed for this purpose. For example, a 30% PERCOLL® gradient centrifugation procedure may be employed (Madan, A. et al. (1999) "Effect of Cryopreservation on Cytochrome P-450 Enzyme Induction in Cultured Rat Hepatocytes, Drug Metab. Dispos. 27(3):327-335; Sun, E. L. et al. (1990) "*Cryopreservation Of Cynomologus Monkey (Macaca fascicularis) Hepatocytes For Subsequent Culture And Protein Synthesis Studies,*" In Vitro Cell Development and Biology 25:147-150; Lawrence, J. N. et al. (1991) "*Development Of An Optimal Method For The Cryopreservation Of Hepatocytes And Their Subsequent Monolayer Culture,*" Toxicology In Vitro, 5(1):39-51; Dou, M. et al. (1992) "*Thawed Human Hepatocytes In Primary Culture,*" Cryobiology 29(4):454-469; Utesch, D. et al. (1992) "*Characterization Of Cryopreserved Rat Liver Parenchymal Cells By Metabolism Of Diagnostic Substrates And Activities Of Related Enzymes,*" Biochemical Pharmacology 44:309-315. For example, the thawed cells may be resuspended in a pre-warmed (approximately 37° C.) 30% PERCOLL® isotonic fractionation buffer and then centrifuged at 100×g at room temperature for twenty minutes to pellet viable cells. The supernatant is discarded and the cells are resuspended in media for a subsequent cryopreservation step directly or for further processing prior to cryopreservation.

Cryopreserved preparations that result from the freezing of a previously frozen-thawed preparation will preferably have a post-thaw cell viability of greater than 50% and more preferably 70% or more. Such high viabilities enable the present invention to accomplish the repeated freezing and thawing of hepatocytes without unacceptable losses of cells or the need for ever greater samples sources.

Pooled Hepatocyte Preparations

The capacity of the present invention to enable the repeated freezing and thawing of hepatocytes additionally facilitates the production of pooled hepatocyte preparations, especially pooled human hepatocyte preparations. As discussed above, individual liver samples yield hepatocytes having differing metabolic capabilities. In order to facilitate the reproducible use or study of hepatocytes, it is desirable to minimize hepatocyte differences attributable to such sample variation by pooling hepatocytes from different sources to obtain a composite or "average" hepatocyte preparation. Such composite hepatocyte preparations may thus be formulated so as to provide a preparation having the metabolic activities of an "average" hepatocyte sample or a preparation whose hepatocyte enzyme functions approximate the hepatocyte enzyme functions of freshly isolated hepatocytes. Such metabolic activities may include, for example, some or all of the following enzymatic activities: coumarin 7-hydroxylase (COUM), dextromethorphan O-demethylase (DEX), 7-ethoxycoumarin O-deethylase (ECOD), activities responsible for the phase II metabolism of 7-hydroxycoumarin (7-HCG and 7-HCS), mephenytoin 4-hydroxylase (MEPH), testosterone 6(β)-hydroxylase (TEST), tolbutamide 4-hydroxylase (TOLB), phenacetin O-deethylase (PHEN), or chlorzoxazone 6-hydroxylase (CZX). The substrates, methods of measurements and assay units for assays of such metabolic activities are provided in Table I.

For example, preferred preparations of pooled hepatocytes will yield assay values within the ranges identified in Table II. Alternatively, the hepatocytes samples used to form the pooled preparation may be selected so as to maximize, minimize, or emphasize certain hepatocyte functions over other functions so as to yield a pooled preparation that exhibits a user desired profile of liver cell function(s).

The pooled hepatocyte preparations of the present invention may comprise hepatocytes obtained from the same source at differing times, or from two or more different sources. Preferably, pooled hepatocyte preparations will result from the pooling of hepatocytes obtained from three, four, five, six or more different sources.

Most preferably, the pooled hepatocyte preparations of the invention will comprise at least one population of hepatocytes that were cryopreserved prior to pooling. For example, a pooled hepatocyte preparation may comprise one or more hepatocyte specimens that were cryopreserved prior to pooling with one or more freshly isolated hepatocyte specimens. Alternatively, a pooled hepatocyte preparation may comprise only hepatocyte specimens that were previously cryopreserved. Table II provides the normal range (i.e., the range between Assay Minimum and Assay Maximum for each Assay). Table II values are derived data of the last 150+ lots of human cryopreserved hepatocytes

TABLE I

Hepatocyte Metabolic Activities

| Abbreviation | Substrate/Assay | Method of Measurement | Units |
|---|---|---|---|
| 7-HCG | 7-hydroxycoumarin glucuronide | Phase II metabolism of 7-hydroxycoumarin | pmol/min/$10^6$ cells |
| 7-HCS | 7-hydroxycoumarin sulfate | Phase II metabolism of 7-hydroxycoumarin | pmol/min/$10^6$ cells |
| NAT1 | p-aminobenzoic acid | N-acetylation of p-aminobenzoic acid | nmol/mg/min |
| NAT2 | Sulfamethazine | N-acetylation of Sulfamethazine | nmol/mg/min |
| VBTY | viability | Trypan Blue ™ exclusion | percentage |
| AP | Alkaline Phosphatase | Sigma kit | units/mg protein |
| GGT | gamma-glutamyl transpeptidase | GGT stain | positive |
| UGT1 | 7-hydroxycoumarin | Phase II metabolism of 7-hydroxycoumarin | 169 pmol/mg/min |
| P450 | cytochrome p450 content | carbon monoxide difference spectrum | Not determined for cryo hepatocytes nmol/mg protein |
| CZX | chlorzoxazone | chlorzoxazone 6-hydroxylation | 31.1 pmol/mg/min* |
| COUM | coumarin | coumarin 7-hydroxylation | 50.0 pmol/mg/min* |
| DEX | dextromethorphan | dextromethorphan O-demethylation | 21.4 pmol/mg/min* |
| MEPH | mephenytoin | mephenytoin 4-hydroxylation | 24.1 pmol/mg/min* |
| PHEN | phenacetin | phenacetin O-deethylation | 28.9 pmol/mg/min* |
| TEST | testosterone | testosterone 6(beta)-hydroxylation | 96.8 pmol/mg/min* |
| TOLB | tolbutamide | tolbutamide 4-hydroxylation | 30.6 pmol/mg/min* |
| PROT | protein content | Pierce protein kit | Not determined for cryo hepatocytes mg/mL |
| ECOD | ethoxycoumarin | 7-ethoxycoumarin O-deethylation | 37.3 pmol/mg/min* |

TABLE II

Hepatocyte Assays

| Assay | Normal Range (pmol/min/$10^6$ cells) |
|---|---|
| coumarin 7-hydroxylation | 1 to 154 |
| Dextromethorphan O-demethylation | 0.5 to 96 |
| 7-ethoxycoumarin O-deethylation | 1 to 154 |
| Phase I metabolism of 7-hydroxycoumarin | 2 to 545 |
| Phase II metabolism of 7-hydroxycoumarin | 0 to 110 |
| mephenytoin 4-hydroxylation | 0.2 to 442 |
| testosterone 6(beta)-hydroxylation | 2 to 675 |
| tolbutamide 4-hydroxylation | 1.8 to 82 |
| phenacetin O-deethylation | 1 to 125 |
| chlorzoxazone 6-hydroxylation | 2 to 215 |

In certain embodiments of the invention, hepatocyte preparations will have assay values in the above stated ranges for at least three of, and preferably for at least four of, still more preferably for at least six of, and most preferably for at least eight of the following assays: the COUM assay; the DEX assay; the ECOD assay; the 7-HCG assay; the 7-HCS assay; the MEPH assay; the TEST assay; the TOLB assay; the PHEN assay; the CZX assay.

If desired, the cryopreserved hepatocytes may be plated on to collagen-coated tissue culture plates, or tissue culture plates coated with other extracelluar matrix proteins including but not limited to laminin, fibronectin, entactin, poly-L-lysine, gelatin, or any combination thereof. Preferably, this is accomplished by diluting an appropriate volume (e.g., 0.2 ml to 2.5 ml) of diluted cells (e.g., cells having a concentration of approximately $0.7 \times 10^6$ cells/ml) onto the plates. For plating on a 96-well microtiter plate, it is desirable to further dilute the cell suspension to a concentration of $0.35 \times 10^6$ cells/ml with InVitroGRO CP medium, and to add 100 µl of the cell suspension to each well. It is preferred to even distribute the cells in the wells. This can be accomplished by gently shaking the plates in a back-and-forth and side-to-side manner; the use of a circular motion will cause the cells to unevenly pool in the center of the wells. Human hepatocytes handled in this manner will attach to the plates in 2-4 hours, however, if minimal handling is desired, the cells can be allowed to attach overnight.

Having now generally described the invention, the same will be more readily understood through reference to the following examples, which are provided by way of illustration and are not intended to be limiting of the present invention unless specified.

EXAMPLE 1

Refreezing of Thawed Hepatocyte Preparations

Cryopreserved hepatocytes are thawed and refrozen as indicated below.

Materials: 30 cc syringe, two couplers, PERCOLL® in a 1 L bag, INVITROGRO™ CP-2 medium in a 2 L bag, 1-2 L autoclaved beaker, heater, waterbath, centrifuge tube rack.

Procedure:
1) Set up a recirculating waterbath heater at 37-42° C.
2) Add approximately 200-400 mls of INVITROGRO™ CP medium to a 1-2 L beaker. Equip Biological Safety Cabinet with a manual pipet or a liquid handling robot.
3) Remove approximately 50 cryovials from dewar receptacle and quickly place them in 2 test tube racks. When possible, space vials apart.
4) Submerge solid cell suspensions into heated waterbath until the ice chunks can be dislodged when the vial is inverted.
5) Pour cell suspension from each vial into the beaker. Add 1 ml of INVITROGRO™ CP medium from the small beaker into each vial to rinse and pour contents into the beaker. Transfer thawed cell suspension into a 1 L sterile bag.
6) Attach bag, INVITROGRO™ CP medium in a 2 L bag and PERCOLL® bagged at 30% onto COBE® automated cell processor(a centrifugal system incorporating a flexible membrane that allows the removal of fluids while spinning through use of a rotating seal, hydraulic pump and flexible membrane) and process according to standard practices.
7) Perform a cell count.
8) Cryopreserve cell suspension.

PERCOLL/REDIGRAD™ (Amersham Biosciences) is employed for the PERCOLL® density centrifugation. PERCOLL® is composed of colloidal silica coated with polyvinylpyrrolidone (PVP). The REDIGRAD™ formulation is also composed of colloidal silica but is covalently coated with silane. These coatings are thought to render the material non-toxic and ideal for use with biological materials. Both particles have a density of 1.13 g/ml. Centrifugation of sample in the presence of PERCOLL/REDIGRAD™ results in the spontaneous formation of a density gradient due to the heterogeneity of particle sizes in the medium.

PERCOLL/REDIGRAD™ is best used in balanced salt solutions, such as physiological saline (0.15 M NaCl), although 0.25 M sucrose may be employed. The addition of 9 parts (v/v) of PERCOLL/REDIGRAD™ to 1 part (v/v) of either 1.5 M NaCl, 10× concentrated cell culture medium, or 2.5 M sucrose will result in a solution adjusted to about 340 mOs/kg $H_2O$. Solutions of different osmotic pressure can be produced by adjusting the relative volumes of PERCOLL/REDIGRAD™ and salt or sucrose solution. (Vincent, R. et al. (1984) "*Adjustment Of The Osmolality Of Percoll For The Isopycnic Separation Of Cells And Cell Organelles,*" Anal. Biochem. 141(2):322-328). The final adjustment to the required osmolality can be carried out by the addition of salts or distilled water. Concentrations other than 10× physiological saline may also be used satisfactorily.

PERCOLL/REDIGRAD™ will form self-generated gradients by centrifugation in fixed-angle rotor heads after 15 minutes. Hepatocytes can be separated by centrifugation at 50-100 $g_{av}$ in fixed-angle or swinging bucket rotor heads after 10-30 minutes.

EXAMPLE 2

Variation of Primary Hepatocyte Samples

To illustrate the sample-to-sample variation of different sources of individual (unpooled) hepatocytes, hepatocytes are isolated from 82 different donors and analyzed for cell viability and enzyme function. The following metabolic activities are evaluated: COUM, DEX, ECOD, 7-HCG, 7-HCS, MEPH, TEST, TOLB, PHEN, and CZX. The results are shown in Table III.

TABLE III

Variation of Hepatocyte Samples

| Lot No. | Sex | %V | COUM | DEX | ECOD | 7-HCG | 7-HCS | MEPH | TEST | TOLB | PHEN | CZX |
|---|---|---|---|---|---|---|---|---|---|---|---|---|
| 067 | M | 62% | 67 | 1 | 70 | 231 | 24 | 2 | 44 | 35 | 27 | 24 |
| 086 | F | 74% | 51 | 23 | 10 | 50 | 9 | 1 | 38 | 13 | BQL | 18 |
| 089 | F | 77% | 25 | 21 | 8 | 23 | 6 | 1 | 11 | 13 | BQL | 29 |
| 090 | F | 74% | 30 | 25 | 7 | 13 | BQL | 2 | 19 | 15 | BQL | 16 |
| 091 | F | 73% | 13 | 29 | 66 | 44 | 10 | 12 | 252 | 36 | 27 | 36 |
| 094 | F | 67% | 41 | 12 | 37 | 24 | 4 | 21 | 126 | 40 | 19 | 87 |
| 099 | F | 86% | 21 | 15 | 7 | 4 | BQL | 1 | 60 | 10 | BQL | 22 |
| 104 | M | 81% | 63 | 21 | 44 | 247 | 25 | 2 | 58 | 37 | 8 | 20 |
| 105 | M | 67% | 59 | 15 | 24 | 38 | 14 | 1 | 29 | 27 | 12 | 27 |
| 110 | F | 77% | 45 | 24 | 35 | 23 | 4 | 6 | 206 | 11 | 54 | 36 |
| 111 | F | 71% | 4 | 10 | 9 | 2 | 3 | 3 | 147 | 2 | 19 | 19 |
| 114 | F | 75% | 39 | 23 | 21 | 10 | 5 | 5 | 59 | TBD | 3 | 45 |
| 122 | M | 79% | 26 | 30 | 29 | 80 | 5 | 1 | 42 | 23 | 4 | 25 |
| 129 | F | 90% | 4 | 24 | 27 | 67 | 18 | 1 | 16 | 33 | 10 | 51 |
| ACU | F | 81% | 53 | 8 | 25 | 74 | 18 | 8 | 80 | 16 | 4 | 23 |
| AIT | F | 83% | 45 | 29 | 13 | 118 | 14 | BQL | 82 | 15 | 11 | 7 |
| AOK | M | 73% | 60 | 21 | 58 | 283 | 64 | 5 | 86 | 30 | 24 | 21 |
| ATR | M | 73% | 7 | 11 | 1 | 39 | 11 | BQL | 11 | 8 | 3 | 4 |
| AVF | M | 70% | 59 | 13 | 50 | 210 | 29 | BQL | 54 | 37 | 11 | 24 |
| BTP | M | 88% | 66 | 29 | 36 | 214 | 25 | 3 | 50 | 45 | 11 | 12 |
| CEC | M | 86% | 47 | 26 | 17 | 105 | 27 | 21 | 32 | 57 | 38 | 36 |
| CEK | F | 80% | 55 | 2 | 39 | 141 | 5 | 16 | 302 | 41 | 7 | 16 |
| CHD | F | 77% | 30 | 14 | 53 | 471 | 42 | 4 | 28 | 23 | 13 | 26 |
| CPN | M | 81% | 28 | 6 | 40 | 100 | 13 | 2 | 168 | 14 | 37 | 21 |
| ECM | M | 85% | 8 | 11 | 10 | 55 | 18 | 6 | 81 | 18 | 21 | 9 |
| EFA | M | 69% | 9 | 9 | 35 | 47 | 5 | 18 | 66 | 12 | 47 | 67 |
| EHI | F | 90% | 88 | 3 | 56 | 291 | 45 | 1 | 248 | 21 | 45 | 43 |
| EJR | F | 75% | 89 | 14 | 32 | 288 | 43 | 8 | 62 | 41 | 1 | 41 |
| ENR | M | 73% | 69 | 28 | 27 | 124 | 31 | 107 | 77 | 36 | 38 | 32 |
| EOB | M | 88% | 14 | 11 | 18 | 65 | 9 | 31 | 49 | 14 | 21 | 35 |
| ETR | F | 88% | 30 | 1 | 34 | 13 | 13 | 7 | 13 | 13 | 37 | 69 |
| EVY | M | 80% | 2 | 20 | 23 | 218 | 77 | 33 | 24 | 25 | 17 | 38 |
| FNL | M | 85% | 17 | 27 | 62 | 282 | 32 | 6 | 6 | 50 | 14 | 24 |
| FRW | M | 75% | 46 | 22 | 16 | 106 | 17 | 48 | 25 | 54 | 44 | 8 |
| GBE | F | 77% | 5 | 49 | 31 | 165 | 20 | 2 | 16 | 19 | 5 | 54 |
| GNG | F | 74% | 57 | 17 | 33 | 54 | 8 | 5 | 95 | 22 | 16 | 22 |
| GTV | F | 71% | 32 | 6 | 8 | 47 | 7 | BQL | 40 | 28 | 16 | 11 |
| GUY | M | 92% | 65 | 12 | 11 | 73 | 12 | 20 | 90 | 13 | 5 | 8 |
| HHG | M | 83% | 2 | 8 | 14 | 251 | 29 | BQL | 28 | 12 | 4 | 40 |
| HRU | M | 90% | 43 | 28 | 39 | 175 | 15 | 4 | 69 | 40 | 57 | 44 |
| ICJ | M | 74% | 134 | 20 | 60 | 287 | 17 | BQL | 129 | 82 | 28 | 7 |
| IEM | M | 88% | 34 | 17 | 23 | 129 | 34 | 72 | 48 | 23 | 19 | 34 |
| IHR | F | 76% | 17 | 43 | 8 | 84 | 9 | 9 | 95 | 46 | 41 | 7 |
| LID | M | 86% | 36 | 31 | 50 | 307 | 54 | 1 | 142 | 49 | 21 | 51 |
| IRX | F | 73% | 57 | 5 | 40 | 172 | 24 | 12 | 113 | 43 | 6 | 18 |
| JUL | M | 82% | 7 | 11 | 3 | 41 | 9 | 7 | 23 | 12 | 2 | 3 |
| KK5 | M | 83% | 1 | 8 | 27 | 319 | 38 | BQL | 61 | 17 | 17 | 42 |
| KPT | F | 83% | 9 | 12 | 32 | 248 | 30 | 55 | 65 | 26 | 56 | 32 |
| KRJ | F | 76% | 6 | 40 | 76 | 359 | 37 | 1 | 11 | 61 | 23 | 20 |
| KRM | F | 78% | 126 | 36 | 55 | 83 | 17 | 103 | 98 | 46 | 74 | 44 |
| K5E | M | 73% | 65 | 27 | 52 | 206 | 74 | 21 | 123 | 42 | 93 | 16 |
| KZO | F | 82% | 38 | 16 | 38 | 262 | 8 | 6 | 75 | 32 | 30 | 20 |
| LAE | M | 76% | 58 | 15 | 50 | 294 | 22 | 14 | 67 | 63 | 125 | 21 |
| MOF | F | 91% | 79 | 17 | 29 | 10 | 12 | 2 | 85 | 5 | 7 | 46 |
| MRS | M | 72% | 119 | 21 | 110 | 450 | 50 | 2 | 675 | 54 | 68 | 28 |
| MTR | F | 69% | 2 | 33 | 23 | 218 | 3 | 5 | 38 | 67 | 39 | 8 |
| MYO | F | 94% | 40 | 24 | 9 | 24 | BQL | BQL | 12 | 7 | BQL | 11 |
| NPX | F | 79% | 36 | 32 | 13 | 130 | 6 | 15 | 76 | 25 | 20 | 10 |
| NQT | M | 85% | 76 | 12 | 39 | 80 | 23 | 2 | 151 | 14 | 20 | 34 |
| OAU | F | 81% | 47 | 26 | 24 | 86 | 8 | 6 | 85 | 46 | 53 | 13 |
| OZL | M | 76% | 16 | 15 | 61 | 300 | 109 | 3 | 165 | 29 | 17 | 43 |
| PFM | F | 87% | 21 | 1 | 11 | 67 | 10 | 3 | 116 | 8 | 15 | 33 |
| PXK | M | 80% | 86 | 35 | 63 | 433 | 78 | 2 | 109 | 62 | 32 | 60 |
| QWG | F | 77% | 16 | 32 | 29 | 300 | 21 | 9 | 50 | 10 | BQL | 15 |
| REL | F | 77% | 40 | 20 | 15 | 109 | 9 | 65 | 100 | 33 | 75 | 10 |
| RFA | F | 78% | 130 | 42 | 49 | 444 | 52 | 6 | 195 | 30 | 28 | 17 |
| RKB | F | 95% | 42 | 16 | 16 | 100 | 8 | 3 | 36 | 17 | 20 | 19 |
| RML | F | 76% | BQL | 6 | 45 | 129 | 31 | 14 | 152 | 24 | 42 | 29 |
| RNG | F | 91% | 119 | 14 | 97 | 298 | 27 | 177 | 207 | 34 | 71 | 41 |
| ROE | F | 82% | 73 | 24 | 36 | 302 | 37 | 2 | 55 | 17 | 2 | 51 |
| SEO | F | 72% | 36 | 25 | 18 | 106 | 9 | 66 | 102 | 50 | 81 | 11 |
| SQJ | F | 74% | 115 | 12 | 100 | 285 | 19 | 175 | 210 | 30 | 81 | 42 |
| SRA | M | 79% | 50 | 6 | 71 | 409 | 84 | 10 | 23 | 28 | 18 | 44 |
| TPZ | F | 83% | 120 | 13 | 101 | 301 | 26 | 171 | 204 | 31 | 82 | 41 |

TABLE III-continued

Variation of Hepatocyte Samples

| Lot No. | Sex | %V | COUM | DEX | ECOD | 7-HCG | 7-HCS | MEPH | TEST | TOLB | PHEN | CZX |
|---|---|---|---|---|---|---|---|---|---|---|---|---|
| TSR | F | 62% | 47 | 66 | 58 | 175 | 20 | BQL | 6 | 77 | 16 | 34 |
| VCM | M | 82% | 42 | 28 | 79 | 415 | 110 | 0.2 | 94 | 16 | 4 | 215 |
| VEN | F | 70% | 79 | 69 | 89 | 328 | 53 | 2 | 32 | 58 | 48 | 81 |
| VTA | M | 78% | 32 | 1 | 25 | 84 | 12 | 5 | 120 | 21 | 40 | 15 |
| WWM | M | 84% | 42 | 1 | 27 | 127 | 12 | 6 | 58 | 21 | 16 | 37 |
| ZAG | M | 85% | 35 | 28 | 39 | 96 | 73 | 1 | 11 | 42 | 17 | 18 |
| ZCR | M | 80% | 84 | 11 | 39 | 160 | 22 | 38 | 14 | 57 | 20 | 18 |
| ZIJ | M | 72% | 6 | 33 | 31 | 320 | 29 | 13 | 25 | 34 | 3 | 13 |

BQL (Below Quantitation Limit)
TBD (To Be Determined)

EXAMPLE 3

Characterization of Pooled Hepatocytes

Cryopreserved pooled lots of hepatocytes are prepared and analyzed for post-thaw viability and enzyme function. The following metabolic activities are evaluated: COUM, DEX, ECOD, 7-HCG, 7-HCS, MEPH, TEST, TOLB, PHEN, and CZX.

Six lots of pooled hepatocytes, comprising either five-donor pools or ten-donor pools, are prepared as described above. Hepatocytes are harvested from individual donors and then cryopreserved as individual lots using liquid nitrogen as freezing agent. Cryopreservation is accomplished by suspending the hepatocytes into freezer-safe vials containing a medium having approximately 10% DMSO and approximately 90% Cryopreservation Medium. The dispensed hepatocytes are then frozen in a controlled rate freezer until a final temperature of approximately −80° C. is reached.

To form the pooled hepatocyte preparations, individual lots are thawed, and the viable cells are isolated by percoll gradient centrifugation. Vials of individual donor cryopreserved hepatocytes were thawed in a 37° C. waterbath (perhaps it would be better to give a range such as 30-40° C. waterbath?) for 60-90 seconds. The thawed cells are decanted into 37° C. media containing 30% Isotonic Percoll and 70% CP-2 media. The cell suspension is centrifuged at 100 g for 20 minutes. The viable cells are recovered in cryopreservation media and counted. The viable cells are diluted to 20 million cells per mL. A second solution containing 20% DMSO and 80% cryopreservation media (equal volume to the cell suspension listed above) is prepared. The 20% DMSO and 80% cryopreservation media is slowly added to the cells suspension mixture. The addition takes 5-10 minutes. The resulting mixture is 10% DMSO, 90% cryopreservation media with cells at 10 million cells per mL. This solution is aliquoted into cryovials at 1.0 mL per vial. The cells are then cryopreserved. Viable cells from individual lots are then pooled to form pooled hepatocyte preparations whose cells have functional assay values within desired ranges.

The pooled lots are then cryopreserved. Table IV below shows the results of the post-thaw viability ("% V") and enzyme function analysis of the pooled lots. As indicated in Table III, pools had an average viability of 79% (S.D. ±6%).

TABLE IV

Summary of Pooled Hepatocyte Lot Data

| Pool | %V | COUM | DEX | ECOD | 7-HCG | 7-HCS | MEPH | TEST | TOLB | PHEN | CZX |
|---|---|---|---|---|---|---|---|---|---|---|---|
| MJI[a] | 89 | 63 | 28 | 66 | 301 | 44 | 12 | 70 | 61 | 50 | 62 |
| YDJ[a] | 72 | 66 | 30 | 80 | 470 | 41 | 1 | 165 | 31 | 27 | 71 |
| APO[b] | 79 | 79 | 21 | 55 | 276 | 43 | 2 | 112 | 22 | 26 | 30 |
| HMB[b] | 76 | 61 | 18 | 70 | 231 | 46 | 3 | 151 | 23 | 20 | 83 |
| IJU[b] | 75 | 32 | 19 | 35 | 232 | 44 | 2 | 124 | 32 | 11 | 42 |
| RKS[b] | 81 | 84 | 20 | 73 | 336 | 53 | 2 | 131 | 28 | 23 | 55 |

[a] 5-donor lots
[b] 10-donor lots

For comparison, Table V below shows summary data for a post-thaw viability and enzyme function analysis of eighty-one individual lots that are cryopreserved (i.e., subjected to one cycle of cryopreservation). This data confirms that the lot-to-lot variability of enzyme function found in individual hepatocyte sources is very high. The data confirms the desirability of employing pooled hepatocyte preparations for providing cryopreserved cells that approximate the enzyme function of "average" hepatocytes for a wide variety of enzymes.

TABLE V

Summary of Pooled Hepatocyte Lot Data

|  | % V | COUM | DEX | ECOD | 7-HCG | 7-HCS | MEPH | TEST | TOLB | PHEN | CZX |
|---|---|---|---|---|---|---|---|---|---|---|---|
| Avg | 79 | 37 | 17 | 51 | 276 | 27 | 8 | 35 | 35 | 15 | 19 |
| High | 95 | 134 | 69 | 110 | 471 | 110 | 177 | 675 | 82 | 125 | 215 |
| Low | 62 | 6 | 1 | 31 | 231 | 24 | 2 | 25 | 34 | 3 | 13 |

EXAMPLE 3

Characterization of the Viability of Pooled Hepatocytes After Thawing

A common use of for cryopreserved hepatocytes is to thaw the hepatocytes and then incubate them with various xenobiotics. For this purpose, it is preferred that the hepatocytes maintain their viability for at least several hours. To examine the post-thaw viability over time for one lot of pooled cryopreserved hepatocytes, the cells were thawed, aliquoted into the wells of a 12-well plate, and incubated at 37° C. with 5% $CO_2$. The viability of the hepatocytes is then measured at time-points for up to six hours. Table VI shows the results of this analysis, wherein, at six hours, 39% of the hepatocytes remained viable

TABLE VI

Post-Thaw Viability Analysis of a Pooled Hepatocyte Lot

| Timepoint | % Viability [a] |
|---|---|
| T = 0 | 88% |
| 0.5 hrs | 79% |
| 1.0 hrs | 84% |
| 2.0 hrs | 79% |
| 3.0 hrs | 73% |
| 4.0 hrs | 67% |
| 6.0 hrs | 69% |

[a] viability determined by Trypan Blue

All publications and patents mentioned in this specification are herein incorporated by reference to the same extent as if each individual publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of producing a desired preparation of multi-cryopreserved hepatocytes, said hepatocytes, being capable of being frozen and thawed at least two times, and in which greater than 70% of the hepatocytes of said preparation are viable after the final thaw, said method comprising:
   (A) subjecting hepatocytes that have been frozen and thawed to density gradient fractionation to separate viable hepatocytes from non-viable hepatocytes,
   (B) recovering the separated viable hepatocytes, and
   (C) cryopreserving the recovered viable hepatocytes to thereby form said desired preparation of hepatocytes without requiring a density gradient step after thawing the hepatocytes for the second time, wherein the hepatocytes are not plated between the first and second cryopreservations, and wherein greater than 70% of the hepatocytes of said preparation are viable after the final thaw.

2. The method of claim 1, wherein said density gradient fractionation comprises density centrifugation through polyvinylpyrrolidone-coated colloidal silica particles.

3. The method of claim 1, wherein said hepatocytes are selected from the group consisting of human hepatocytes, porcine hepatocytes, simian hepatocytes, canine hepatocytes, feline hepatocytes, bovine hepatocytes, equine hepatocytes, ovine hepatocytes and rodent hepatocytes.

4. The method of claim 3, wherein said hepatocytes are human hepatocytes.

5. The method of claim 1, wherein said preparation comprises a pooled preparation of hepatocytes of multiple sources.

6. The method of claim 5, wherein said multiple sources are of the same gender, race, or health state.

7. The method of claim 5, wherein the hepatocytes of said pooled preparation of hepatocytes provide said pooled preparation with a desired level of a metabolic activity.

8. The method of claim 7, wherein said metabolic activity is selected from the group consisting coumarin 7-hydroxylase (COUM), dextromethorphan O-demethylase (DEX), 7-ethoxycourmarin O-deethylase (ECOD), activities responsible for the phase II metabolism of 7-hydroxycoumarin (7-HCG and 7-HCS), mephenytoin 4-hydroxylase (MEPH), testosterone 6(β)-hydroxylase (TEST), tolbutamide 4-hydroxylase (TOLB), phenacetin O-deethylase (PHEN), and chloroxazone 6-hydroxylase (CZX).

9. The method of claim 1, wherein greater than 80% of the hepatocytes of said preparation are viable.

10. A method of investigating in vitro drug metabolism comprising incubating hepatocytes of a multi-cryopreserved hepatocyte preparation in the presence of a xenobiotic, and determining the metabolic fate of the xenobiotic, or the affect of the xenobiotic on the hepatocytes or on an enzyme or metabolic activity thereof, wherein the hepatocytes have been frozen and thawed at least two times, and wherein greater than 70% of the hepatocytes of said preparation are viable without requiring a density gradient step after thawing the hepatocytes for the second time, wherein the hepatocytes are not plated between the first and second cryopreservations.

11. The method of claim 5, wherein said multiple sources are of different gender, race or health state.

* * * * *

UNITED STATES PATENT AND TRADEMARK OFFICE
CERTIFICATE OF CORRECTION

| | | |
|---|---|---|
| PATENT NO. | : 7,604,929 B2 | Page 1 of 1 |
| APPLICATION NO. | : 11/110879 | |
| DATED | : October 20, 2009 | |
| INVENTOR(S) | : Daniel Dryden et al. | |

It is certified that error appears in the above-identified patent and that said Letters Patent is hereby corrected as shown below:

Title page, item (*) Notice: should read as follows: Subject to any disclaimer, the term of this patent is extended or adjusted under 35 U.S.C. 154(b) by 433 days.

At column 19, line 26, please change "39%" to --69%--.

Signed and Sealed this

Fifteenth Day of June, 2010

David J. Kappos
*Director of the United States Patent and Trademark Office*

(12) EX PARTE REEXAMINATION CERTIFICATE (8874th)
United States Patent
Dryden et al.

(10) Number: US 7,604,929 C1
(45) Certificate Issued: *Feb. 28, 2012

(54) CELLULAR COMPOSITIONS AND METHODS FOR THEIR PREPARATION

(75) Inventors: Daniel Dryden, Westminter, MD (US); James Hardy, Ijamsville, MD (US)

(73) Assignee: KBC Bank NV, London (GB)

Reexamination Request:
No. 90/011,276, Oct. 8, 2010

Reexamination Certificate for:
Patent No.: 7,604,929
Issued: Oct. 20, 2009
Appl. No.: 11/110,879
Filed: Apr. 21, 2005

(*) Notice: This patent is subject to a terminal disclaimer.

Certificate of Correction issued Jun. 15, 2010.

(51) Int. Cl.
*A01N 1/00* (2006.01)
*C12N 5/00* (2006.01)
*C12N 5/08* (2006.01)

(52) U.S. Cl. .......... 435/1.1; 435/1.3; 435/370; 435/374; 435/375

(58) Field of Classification Search .............. None
See application file for complete search history.

(56) References Cited

To view the complete listing of prior art documents cited during the proceeding for Reexamination Control Number 90/011,276, please refer to the USPTO's public Patent Application Information Retrieval (PAIR) system under the Display References tab.

*Primary Examiner* — Sharon Turner

(57) ABSTRACT

The present invention relates to novel cell (e.g., hepatocyte, etc.) compositions and methods for their preparation and use. In particular, the invention concerns methods of processing preparations of such cells so as to permit their repeated cryopreservation and thawing while retaining substantial viability. The invention also concerns preparations of cells (e.g., hepatocytes) that have been repeatedly cryopreserved and thawed.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1-9 and 11 is confirmed.

Claim 10 is cancelled.

* * * * *